US005679833A

United States Patent [19]
Benn et al.

[11] Patent Number: 5,679,833
[45] Date of Patent: Oct. 21, 1997

[54] SYNTHESIS OF VINYL ESTERS

[75] Inventors: Gerald Philip Benn; Janet Catrine Doyle; Peter Stuart Littlewood, all of West Yorkshire, United Kingdom

[73] Assignee: Allied Colloids Limited, West Yorkshire, United Kingdom

[21] Appl. No.: 604,953

[22] PCT Filed: Sep. 15, 1993

[86] PCT No.: PCT/GB93/01953

§ 371 Date: Feb. 28, 1996

§ 102(e) Date: Feb. 28, 1996

[87] PCT Pub. No.: WO95/07879

PCT Pub. Date: Mar. 23, 1995

[51] Int. Cl.$^6$ ............................................. C07C 67/14
[52] U.S. Cl. ........................................ 560/213; 560/130
[58] Field of Search .............................. 560/213, 130

[56] References Cited

U.S. PATENT DOCUMENTS

| | | | |
|---|---|---|---|
| 2,028,012 | 1/1936 | Reid | 260/106 |
| 2,890,241 | 6/1959 | Holmen | 560/213 |
| 4,068,082 | 1/1978 | Stoffey | 560/90 |

FOREIGN PATENT DOCUMENTS

| | | | |
|---|---|---|---|
| 61-286346 | 12/1986 | Japan | C07C 69/54 |
| 61-286347 | 12/1986 | Japan | C07C 69/653 |
| 890214 | 1/1959 | United Kingdom . | |

*Primary Examiner*—C. Warren Ivy
*Assistant Examiner*—Jean F. Vollano
*Attorney, Agent, or Firm*—Sughrue,Mion,Zinn,Macpeak & Seas, PLLC

[57] ABSTRACT

Vinyl ester of an alcohol (such as benzoin) is made by reaction of the alcohol with a 3-haloalkyl acid halide (such as 3-chloropropional chloride or bromide) in an anhydrous liquid reaction medium comprising an aprotic solvent (such as toluene) and a hydrogen halide acceptor (such as a tertiary amine) at a temperature of at least 20° C.

11 Claims, No Drawings

SYNTHESIS OF VINYL ESTERS

This invention relates to the synthesis of vinyl esters derived from an alcohol which may be aliphatic or non-aliphatic (e.g., a phenol) and may be polyhydric. The invention is of particular value when the alcohol is sterically hindered due to the position of the hydroxyl group of the alcohol relative to a cyclic or other bulky group in the alcohol.

When the alcohol that is to provide the esterifying group is not sterically hindered (for instance when it is a straight chain aliphatic alcohol) it is relatively easy to form a vinyl ester by reaction of the alcohol with an ethylenically unsaturated carboxylic acid, for instance using an acidic catalyst. However this technique tends to be inadequate when the alcohol is sterically hindered.

One example of a valuable ester that is difficult to synthesise is benzoin acrylate. The hydroxyl group in benzoin is sterically hindered and the solubility of benzoin in many solvents is low. A synthesis of benzoin acrylate is described in Chemical Abstracts 40151K Volume 68 in which benzoin was dissolved in dimethyl aniline and chloroform and acryloyl chloride was added dropwise at below 10° C. The recovery procedures involve distillation under reduced pressure and the addition of aqueous sulphuric acid with ice cooling. The use of acryloyl chloride as a reactant is undesirable because of difficulties associates with the manufacture, supply and storage of acryloyl chloride. For instance its initial synthesis is inconvenient to perform and the product tends to be unstable on storage.

A further disadvantage in the described process is that it requires the use of chloroform as part of the reaction medium. This may result in the end product containing trace amounts of chloroform. For some purposes, e.g., pharmaceutical purposes, even trace amounts of halogenated hydrocarbon impurities are considered undesirable.

Processes are described in JP-A-61/286346 and 61/286347 in which one mole of a particular sterically hindered alcohol is reacted with 0.9 to 1.25 moles β chloropropionyl chloride per hydroxyl group at −10° to 35° C. in a polar organic solvent and in the presence of an aqueous solution of sodium hydroxide or potassium hydroxide. Temperatures of 0° to 10° C. are said to be especially preferred. It is stated that if the temperature is higher, there is hydrolysis of the chloropropionol chloride which causes a decline in yield, and there is hydrolysis of the end product.

Although the low temperatures are essential in this process for the reasons stated, they have undesirable disadvantages. The solubility of the alcohol at the low temperatures is less than it would be at higher temperatures. With alcohols such as benzoin, which tend to have a relatively low solubility in many solvents, the use of low temperatures necessarily limits the concentration of the alcohol that can be dissolved in the reaction mixture, and thus reduces the yield of vinyl ester that can be obtained from a given reaction vessel in a given reaction time (the pot yield). Further, the use of a low temperature necessarily results in a lower reaction rate.

One important object of the invention is to provide a more convenient and reliable synthesis of benzoin acrylate.

Another object of the invention is to provide a convenient synthesis for vinyl esters of alcohols in general, especially sterically hindered alcohols.

Another object is to provide such processes that can be performed in the absence of halocarbons.

Another object to devise a process for making vinyl esters of alcohols and which is convenient to perform and which is especially suitable for sterically hindered alcohols and which is capable of giving a good pot yield of the desired product.

In the invention, we make a vinyl ester of an alcohol by reaction of the alcohol with a 3-haloalkyl acid halide in a liquid reaction medium in which the alcohol is dissolved and through which a hydrogen halide acceptor is distributed, and in this process the liquid reaction medium is an anhydrous reaction medium and comprises aprotic solvent, and the reaction temperature is at least 20° C.

As a result of the reaction medium being anhydrous and comprising a aprotic solvent and the hydrogen halide acceptor it is possible to perform the reaction at sufficiently high temperature that even relatively insoluble alcohol such as benzoin can have reasonably high solubility (e.g., at least 10%) and such that a satisfactory rate of reaction is achieved. Accordingly it is possible, by the invention, to obtain a high pot yield rapidly with little or no by-product formation.

The reaction temperature is normally above 35° C. and most preferably it is above 40° C. The upper limit will generally depend on, for instance, the thermal stability of the alcohol and the vinyl ester, the boiling point of the solvent, and on the reaction apparatus that is being used. Generally the reaction temperature is below 90° C. For many reactions, temperatures in the range of 45° to 80° C. are convenient. Preferably the reaction is conducted with reflux distillation of the solvent and so the solvent and the reaction pressure (which is generally at or below atmospheric) may be selected to give a suitable reflux and reaction temperature.

It is essential that the reaction medium is anhydrous since the presence of significant amounts of water will result in hydrolysis of the acid halide group and in increased by-product formation. Preferably the amount of water in the reaction medium during the reaction is as low as possible and should be substantially zero. However very small amounts, e.g., 1%, may be tolerated, but increasing the amount of water tends to increase the amount of by-products. The haloalkyl acid halide can be used to dehydrate the reaction medium (with consequential and generally undesirable formation of hydrolysis products) but generally each of the components that is to be used in the reaction medium should be substantially anhydrous. If any component is likely to be contaminated with moisture it is desirable to subject that component to a dehydration process before introduction to the reaction, for example by exposure to a material that will remove water. This may be a material that will absorb water reversibly but is preferably a scavenger that will react irreversibly with water. Suitable scavengers are acid anhydrides, acid chlorides and, especially, phosphorous pentoxide.

In order to ensure the maintenance of anhydrous conditions throughout the reaction it is often preferred to include a water scavenger, such as phosphorous pentoxide, in the reaction medium.

The hydrogen halide acceptor may be any material that will absorb hydrogen halide liberated during the reaction, and in particular is a material that will promote the extraction of hydrogen halide from the starting material or intermediate product, which is probably the haloalkyl ester of the alcohol. The hydrogen halide acceptor must be distributed throughout the reaction medium in order that it is readily available to accept hydrogen halide as it is liberated. It can be present as finely dispersed solid material, for instance an inorganic base such as sodium or potassium carbonate or bicarbonate, in which event the reaction with the hydrogen halide is a solid phase reaction. Preferably, however, the hydrogen halide acceptor is in solution in the reaction medium, and the reaction is a liquid phase reaction. The preferred hydrogen halide acceptors are tertiary amines where the nitrogen atom is substituted by three groups selected from aliphatic, cycloaliphatic, heterocyclic and aromatic groups, preferably a tertiary alkylamine where each alkyl group contains 1 to 8 carbon atoms. Triethylamine is a suitable hydrogen halide acceptor. The acceptor should be unreactive with the alcohol and the 3-haloalkyl acid halide.

The aprotic solvent can be any solvent that is free of a proton that could result in reaction between the solvent and the acid halide. Preferably it is a solvent of moderate polarity for instance having a Hildebrand polarity of less than 0.6. It can be an ether (for instance tetrahydrofuran) or ketone (for instance acetone) but is preferably a solvent of low polarity, preferably a non-polar solvent. Although a halogenated hydrocarbon such as dichloromethane can be used as part or all of the the solvent, it is preferred for the solvent and the reaction medium to be free of halo carbons. Preferably the aprotic solvent is a hydrocarbon solvent. The hydrocarbon may be aliphatic, alicyclic or aromatic, especially a petroleum ether, paraffin, toluene or xylene. Preferably the reaction medium consists only of the defined solvent or solvents and reactants, so that the defined aprotic solvent is preferably the only solvent that is present in the reaction.

The amount of aprotic solvent will be selected having regard to the reaction temperature that is to be used and the solubility of the alcohol in the aprotic solvent. Generally the reaction temperature and solvent are such that the alcohol has a solubility of at least 10% by weight in the solvent at the chosen reaction temperature (based on the weight of alcohol and the aprotic solvent) and so the amount of aprotic solvent will generally be below 10 parts by weight per part by weight of the alcohol. In order to maximise pot yield, the amount is generally as low as is acceptable consistent with the solubility of the alcohol, and typically is below 7 parts per part by weight alcohol. Generally it is above 2 parts.

When the hydrogen halide acceptor is dissolved in the reaction medium, the concentration of the alcohol in the liquid phase of the reaction medium is generally at least 8%, and preferably at least 12 or 15% (based on the weight of alcohol and liquid reaction medium) at the reaction temperature.

The proportions of alcohol and acid halide and hydrogen halide acceptor are preferably substantially stoichiometric. The amount of halo halide is generally from 0.8 to 2 moles per mole hydroxyl groups in the alcohol, with amounts of 1 to 1.4 moles being suitable. The amount of hydrogen halide acceptor is generally from 2 to 3 moles per mole hydroxyl groups in the alcohol, although greater amounts can be used.

The 3-haloalkyl acid halide is generally a compound of the formula $CR_2^1XCHR^2COY$. The groups $R^1$ may be the same or different and can be aliphatic, heterocyclic or aromatic. For instance they can be C1-8 alkyl, phenyl or benzyl. Preferably at least one group $R^1$, and frequently each of the groups $R^1$, is hydrogen. $R^2$ can be methyl but is generally hydrogen. X and Y can be the same or different and may be chloro or bromo. The preferred compound has X and Y chloro and each $R^1$ and $R^2$ hydrogen, namely 3-chloro propionyl chloride.

The alcohol is preferably a sterically hindered alcohol. Generally it contains at least 4 carbon atoms and more usually at least 10 carbon atoms. It can be monohydric or polyhydric (e.g., a glycol or sugar) and it can be aliphatic, heterocyclic or aromatic (e.g., a phenol).

The alcohol can be selected from cyclic alcohols, as described below, tertiary alcohols as described below, and primary or secondary alcohols as described below.

The cyclic alcohols are alcohols in which the hydroxyl group is bonded to a ring carbon atom. The ring may be aliphatic, aromatic or heterocyclic and generally contains 5 to 8 ring members or may be a bicyclic or other polycyclic ring. The cyclic alcohol may include more than one hydroxyl group. It may be a sugar.

The tertiary alcohols are alcohols in which the hydroxyl group is bonded to a tertiary carbon atom. This is substituted by three groups which are selected from aliphatic, aromatic and heterocyclic groups and which generally provide, together, at least 4 and usually at least 10 carbon atoms.

The primary and secondary alcohols are alcohols wherein the hydroxyl group is bonded to a carbon atom carrying one or two hydrogens and substituted by two or one aliphatic, aromatic or heterocyclic groups wherein at least one of the substituents comprises a tertiary carbon atom or a ring of at least five atoms wherein the tertiary carbon or the ring is connected to the primary or secondary carbon by a direct bond or by a chain of up to three atoms.

When the alcohol is monohydric, it can be expressed as having the formula $R^3OH$ in which event the vinyl ester will have the formula $CR_2^1{=}CR^2COOR^3$, but when the alcohol is dihydric having the formula $HOR^3OH$ the end product may be a compound having the formula $CR_2^1{=}CR^2COOR^3OOCCR^2{=}CR_2^1$ or it may be an unsymmetrical compound, for instance wherein one of the hydroxyl groups does not react.

For simplicity, in the following description we refer only to monohydric alcohols but it will be appreciated that dihydric or polyhydric alcohols can be used.

The alcohol $R^3OH$ is preferably a compound of the formula

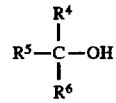

wherein $R^4$, $R^5$ and $R^6$ are preferably as defined below, and $R^3$ in the desired end product therefore preferably is a group of the formula

In the preferred cyclic alcohols $R^4$ and $R^5$ together with the carbon atoms to which they are attached provide a ring of at least 5 ring atoms that may be aliphatic, heterocyclic or aromatic and $R^6$ is hydrogen or an aliphatic, aromatic or heterocyclic group or is absent if the ring is unsaturated. The ring may itself be a ring in a polycyclic compound, for instance at least one other ring may be fused to it. Suitable examples of cyclic alcohols of this type include 1 methyl cyclohexanol, substituted phenols, hydroxypyridine.

In the preferred tertiary alcohols, $R^4$, $R^5$ and $R^6$ are each aliphatic, aromatic or heterocyclic. It is particularly preferred that at least one of them should be a group $R^7$ as defined below.

In preferred secondary alcohols, $R^6$ is hydrogen, $R^5$ is aliphatic, aromatic or heterocyclic and may be a group $R^7$, and $R^4$ is a group $R^7$ as defined below. In primary alcohols $R^5$ and $R^6$ are hydrogen and $R^4$ is a group $R^7$ as defined below.

Groups $R^7$ are groups of the formula

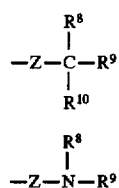

In these, Z is a direct bond or a chain of up to three chain members. These may be carbon (for instance methylene or carbonyl groups) or oxygen (ether linkages) or any other suitable linking groups. Preferably there are only one or two chain members or a direct bond. $R^8$ and $R^9$ together with the carbon or nitrogen atom to which they are attached may form a ring of at least 5 ring atoms or $R^8$ and $R^9$ may both be aliphatic, aromatic or heterocyclic. In some instances, especially when Z is a direct bond or a single group such as methylene or carbonyl and $R^8$ is a bulky group such as a cyclic group, $R^9$ may be hydrogen. $R^{10}$ is absent when $R^8$ and $R^9$ form an aromatic ring with the carbon atom, but otherwise $R^{10}$ is generally aliphatic, aromatic or heterocyclic, but may be hydrogen, especially when $R^8$ and/or $R^9$ are cyclic or other bulky groups.

Any of the aliphatic groups may be saturated or unsaturated such as alkyl or alkenyl. They may be linear or branched. They generally contain 1 to 24 carbon atoms. Any of the aromatic groups may be wholly aromatic or may comprise aromatic groups substituted on to an aliphatic group and may comprise aliphatic or other substituents on the aromatic group. For instance phenyl groups may be substituted on to methylene and/or may be substituted by halo, alkyl or nitro. In heterocyclic groups, the hetero atoms may be, for instance, oxygen or nitrogen and the ring may contain sufficient carbon atoms to make a 5- or 6-membered ring. This ring may be fused to a carbocyclic or other ring. Any carbocyclic ring generally has 5- or 6-ring carbon atoms and may be fused to other rings.

Preferred alcohols are those in which $R^4$, and optionally also $R^5$, are represented by a group $R^7$ wherein $R^8$ and $R^9$ and the carbon atom to which they are attached form an aromatic ring and $R^{10}$ is absent, and Z is either a direct bond or a carbonyl linkage or other suitable short linkage between the alcoholic carbon and the ring. Such a material is benzoin.

Other examples of suitable alcohols are di- and triphenyl methanols and 2,6-dimethyl-4-heptanol.

The reaction is typically conducted by forming the anhydrous liquid reaction medium of alcohol, aprotic solvent and hydrogen halide acceptor to the desired anhydrous state (e.g., by including a water scavenger or by, if necessary, contacting one or more of the materials with a dehydration agent) and then adding the acid halide gradually to the reaction medium, with the reaction generally being at the desired reaction temperature throughout the addition. Reaction is generally continued for a further period of at least quarter of an hour, e.g., 1 to 5 hours, after the addition is completed. The addition may be conducted over a period of half an hour to eight hours. The reaction is generally continued until subtantially complete conversion is achieved.

After the reaction has been completed, the desired end product is recovered. Recovery can be by filtration (for instance to remove solid phase hydrogen halide acceptor or amine hydrogen halide salt that is in solid state) but preferably the desired end product is recovered by cooling and adding sufficient water to dissolve the amine hydrogen halide salt which can be decanted. The desired ester remains in the aprotic solvent. After washing the organic solution with water, the water is preferably removed by azeotropic or other distillation, or by the use of drying agents. The product can be recrystallised if necessary by conventional techniques.

The following are examples Of the invention.

EXAMPLE 1

Benzoin (180 g), phosphorous pentoxide (4 g) and triethylamine (188 g) were stirred in dry toluene (970 g) and heated to 40° C. The 3-chloropropionyl chloride (131 g) was added dropwise over 4 hours, keeping the temperature below 60° C. After addition was complete the reaction was continued for a further 3 hours and tehn allowedd to cool to ambient. Water (188 g) was added with stirring to dissolve the triethylamine hydrochloride salt. The aqueous phase was separated and the organic extract washed with water (80 g). The combined aqueous layers were backwashed with toluene (167 g).

The combined organic phases were returned to the reaction flask and water was removed by azeotropic distillation followed by removal of the solvent under vacuum to leave 220 g (97.8%) of crude dark yellow product. Recrystallisation gave 169 g of a fine yellow powder.

EXAMPLE 2

This example demonstrates that alcohols can be acrylated by halogenated propionyl chlorides other than the chlorinated reagent. The procedure of Example 1 is employed but using 3-bromopropionyl chloride, the conversion of benzoin into benzoin acrylate being 89%.

EXAMPLES 3 TO 7

Acrylate esters were prepared from several hindred alcohols following the same procedure as described in Example 1. The alcohols used were phenol, 2,6-di-t-butyl-4-methylphenol, diphenylmethanol, triphenylmethanol and 2,6-dimethyl-4-heptanol and the results obtained are shown in the following table where "Yield of Product" indicates the yield of acrylate ester based on starting alcohol.

TABLE

| Example | Starting Alcohol | Reaction Time (h) | Yield of Product (%) |
|---|---|---|---|
| 3 | Phenol | 1 | 96 |
| 4 | 2,6-di-t-butyl-4-methylphenol | 2 | 73 |
| 5 | Diphenylmethanol | 1 | 98 |
| 6 | Triphenylmethanol | 1 | 72 |
| 7 | 2,6-Dimethyl-4-heptanol | 1 | 95 |

EXAMPLE 8

This example demonstrates a process broadly similar to Example 1 but using dichloromethane instead of toluene.

Benzoin (57 g), phosphorus pentoxide (1.7 g) and triethylamine (59.9 g) were stirred in dry dichloromethane (200 cm³) and heated to reflux after which 3-chloropripionyl chloride (42.8 g) was added dropwise over 40 min. After addition was complete the reaction was continued for a further 60 min before being allowed to cool to ambient and ater (50 cm³) added with stirring to dissolve the triethylammonium chloride. The aqueous phase was separated and the organic extract washed with water (50 cm³). The combined aqueous layers were then backwashed with dichloromethane (30 g).

The combined organic phases were returned to the reaction flask and water was removed by distillation of the azeotrope with dichloromethane. The solvent was removed by distillation to give 70 g (97.9%) of a crude dark yellow product. Recrystallisation yielded 58.6 g of a fine yellow powder.

Because dichloromethane can result in halo carbon residues in the end product in trace amounts, and because its use necessitates extensive recovery procedures, this process is much less satisfactory than the process of the preceding examples. It is significant that although toluene might have been expected to be a less efficient solvent in the reaction, the yield in example 1 is substantially the same as in example 8 using dichloromethane, and thus the invention has the advantage of giving results using toluene that are as good as can be obtained using dichloromethane, combined with the avoidance of the disadvantages of halo carbons.

We claim:

1. A process for making a vinyl ester of an alcohol by reaction of the alcohol with a 3-haloalkyl acid halide in a liquid reaction medium in which the alcohol is dissolved and through which a hydrogen halide acceptor is distributed, characterised in that the liquid reaction medium is anhydrous and comprises aprotic solvent and the reaction temperature is at least 20° C.

2. A process according to claim 1 in which the reaction temperature is at least 40° C.

3. A process according to claim 1 in which the reaction medium is free of halo carbon and the aprotic solvent is a hydrocarbon solvent.

4. A process according to claim 1 in which the reaction medium includes a water scavenger.

5. A process according to claim 1 in which the reaction medium includes phosphorous pentoxide as a water scavenger.

6. A process according to claim 1 in which the reaction temperature and the aprotic solvent are such that the alcohol has a solbility of at least 10% by weight in the solvent at the reaction temperature (based on the weight of alcohol and aprotic solvent).

7. A process according to claim 1 in which the alcohol is selected from cyclic alcohols, tertiary alcohols, and primary or secondary alcohols substituted by at least one aliphatic, aromatic or heterocyclic group that comprises a tertiary carbonatom or a ring of at least five atoms wherein the tertiary carbon atom or the ring is connected to the primary or secondary carbon of the primary or secondary alcohol by a direct bond or by a chain of up to three atoms.

8. A process according to claim 7 in which the alcohol is benzoin.

9. A process according to claim 1 in which the hydrogen halide acceptor is dissolved in the liquid reaction medium and is a tertiary amine.

10. A process according to claim 1 in which the 3-haloalkyl acid halide is 3-halo propionyl halide where each of the halogen atoms is individually selected from chlorine and bromine.

11. A process according to claim 1 for making benzoin acrylate comprising reacting 1 mole benzoin at 40° to 80° C. with 0.8 to 2 moles 3-chloro or 3-bromo propionyl chloride or bromide while dissolved in an anhydrous reaction medium that is free of halo carbon and that comprises a hydrocarbon solvent and a tertiary amine hydrogen halide acceptor.

* * * * *